US00PP10631P

United States Patent [19]

Delbard

[11] Patent Number: Plant 10,631

[45] Date of Patent: Oct. 6, 1998

[54] HYBRID TEA ROSE PLANT NAMED 'DELSTRORANGE'

[75] Inventor: Guy Delbard, Hyeres, France

[73] Assignee: Societe Anonyme Des Pepinieres et Roseraies Georges Delbard, Commentry, France

[21] Appl. No.: 800,067

[22] Filed: Feb. 14, 1997

[30] Foreign Application Priority Data

Dec. 19, 1996 [FR] France ..... 15221

[51] Int. Cl.[6] ..... A01H 5/00

[52] U.S. Cl. ..... Plt./13

[58] Field of Search ..... Plt./11, 12, 13

[56] References Cited

PUBLICATIONS

UPOV–ROM, Apr. 1997 Plant Variety Database, GTI Jouve Retrieval Software, citation for 'Delstrorange'.

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that abundantly forms attractive double flowers that are pink striped with white. Such flowers exhibit a good vase life and possess petals that detach cleanly. The plant exhibits a bushy growth habit, forms relatively straight stems, forms semi-vigorous to vigorous vegetation, and is particularly well suited for greenhouse forcing for cut flower production. Additionally, the plant is resistant to diseases when grown under greenhouse conditions or when grown outside in the garden.

1 Drawing Sheet

SUMMARY OF THE INVENTION

The new variety is a mutation of unknown causation of the 'Delstrobla' variety U.S. Plant Pat. No. 9,037). Such new variety was discovered during June 1994 while growing among plants of the 'Delstrobla' variety in a greenhouse at Hyéres, France. The new variety of the present invention is believed to be a whole plant mutation of the parent 'Delstrobla' variety that was of unknown causation. Had I not discovered and preserved the plant of the new variety it would have been lost to mankind.

It was found through careful study that the new variety of the present invention exhibits the following combination of characteristics:

(a) from a physical point of view forms green mature wood, assumes a bushy growth habit, and forms attractive pink striped with white double flowers, and (b) from the biological point of view forms semi-vigorous to vigorous vegetation, produces flowers in abundance, exhibits the ability readily to be forced, and is resistant to diseases when grown in a greenhouse and in the garden.

The blossom coloration tends to be relatively stable with the passage of time for a given floral crop. However, slight variation in blossom coloration may result when unusual environmental conditions are encountered (e.g., a little more pink or a little more orange coloration).

The new variety well meets the needs of the horticultural industry and is particularly well suited for growing in the greenhouse for the production of attractive cut flowers that are pink striped with white.

The new variety of the present invention can be readily distinguished from other striped Hybrid Tea rose varieties. For instance, the blossoms of the parent 'Delstrobla' variety (U.S. Plant Pat. No. 9,037) are Red-Purple Group 58B and 58C striped with Red Group 55B, 55C, and 55D or white. On the contrary the blossoms of the new 'Delstrorange' variety are Red Group 52A, 52B, and 52C striped with white. Also, the production of the new variety is slightly higher (e.g., approximately 15 percent higher) and the bud size before the calyx breaks is slightly smaller.

The new variety of the present invention exhibits medium and relatively straight stems, rigid and substantially straight peduncles, an excellent ability to be forced under greenhouse conditions, and a good vase life for its distinctive pink striped with white blossoms.

The new variety has been found to undergo asexual propagation and can be readily reproduced by conventional routes, such as budding (i.e., eye grafting) and tissue culture. This asexual reproduction by budding and tissue culture as performed at Hyéres, France, has demonstrated that the characteristics of the new variety are strictly transmissible from one generation to another and are fimly fixed.

The new variety has been named the 'Delstrorange' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

FIG. 1—illustrates a specimen of a leaf with five leaflets—plan view—upper surface;

FIG. 2—illustrates a specimen of a leaf with seven leaflets—plan view—upper surface;

FIG. 3—illustrates a specimen of a leaf with seven leaflets—plan view—under surface;

FIG. 4—illustrates a specimen of a leaf with nine leaflets—plan view—upper surface;

FIG. 5—illustrates a specimen of a young shoot;

FIG. 6—illustrates a specimen of a flowering stem;

FIG. 7—illustrates a specimen of a main branch;

FIG. 8—illustrates a specimen of a floral bud at the opening of the sepals;

FIG. 9—illustrates a specimen of a floral bud in a more advanced stage of opening than as illustrated in FIG. 8;

FIG. 10—illustrates a specimen of a floral bud at the opening of the petals;

FIG. 11—illustrates a specimen of a flower at an early stage in the course of opening;

FIG. 12—illustrates a specimen of a flower in a more advanced stage of opening than as illustrated in FIG. 11;

FIG. 13—illustrates a specimen of a flower in a more advanced stage of opening than as illustrated in FIG. 12;

FIG. 14—illustrates a specimen of an open flower —plan view—reverse;

FIG. 15—illustrates a specimen of an open flower —plan view —obverse;

FIG. 16—illustrates a specimen of a fully open flower—plan view—reverse;

FIG. 17—illustrates a specimen of a fully open flower—plan view—obverse;

FIG. 18—illustrates a specimen of a floral receptacle showing the arrangement of the stamens and pistils; and FIG. 19—illustrates a specimen of a floral receptacle showing the arrangement of the pistils (stamens removed).

DETAILED DESCRIPTION

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height*.—Plants which were pruned to a height of 1 m. produce floral stems having a length of approximately 40 to 70 cm., and an average length of approximately 50 cm.

*Habit*.—Bushy.

Branches:

*Color*.—Young shoots: when approximately 20 cm. long, on the upper part exhibit a reddish-purple coloration, Greyed-Purple Group 183B, then green coloration, Yellow-Green Group 146B with some reddish coloration. Floral stems: Yellow-Green Group 146B. Mature wood: Yellow-Green Group 146B.

*Thorns*.—Configuration: slightly concave on the upper edge and concave on the under edge. Quantity: on a 10 cm. length of a floral stem there commonly are approximately 8 thorns. Length: approximately 9 mm. on average on floral stems and approximately 8 mm. on average on mature wood. Size: commonly range from approximately 1 to 10 mm. in length on floral stems and mature wood. Color: on young shoots of approximately 30 cm. in length, the thorns are Yellow-Green Group 152D with some reddish coloration, and on mature wood the thorns are Greyed-Orange Group 177A (havana brown).

*Leaves*.—Number: typical for the class. Size: medium. Stipules: adnate, medium and typical for the class.

*Leaflets*.—Number: rarely 3, commonly 5 and 7, and rarely 9. Size: medium. Shape: obtuse to rounded at the base of the terminal leaflet; slightly convex in the cross-section; and weak in margin undulation. Serration: present, very small, irregular, and with some purple coloration on the edge. General appearance: medium thickness and medium to strong glossiness on the upper surface of the leaflets. Petiole: the inner surface is grooved with non-glandular edges. Peitole color on young shoot: on the inner surface Greyed-Purple Group 183B and on the outer surface green with some reddish coloration. *Petiole color on floral stem: on the inner surface bronze with green and on the outer surface Yellow-Green Group* 146B, Petiole color on mature wood: on the inner surface Yellow-Green Group 146B and on the outer surface Yellow-Green Group 146C. Petiole length of terminal leaflet: approximately 14 to 19 mm., approximately 16 mm. on average, with a standard deviation of 2 mm. Terminal leaflet length: approximately 42 to 80 mm., approximately 57 mm. on average, with a standard deviation of 10 mm. Terminal leaflet width: approximately 28 to 49 mm., approximately 39 mm. on average, with a standard deviation of 10 mm. Terminal leaflet shape at base: obtuse to rounded. Leaflet color of young shoot: the upper surfaces of the first leaves are green with purple coloration becoming completely green, Yellow-Green Group 146A with purple serrations, and the under surfaces of the first leaves are Greyed-Purple Group 183B becoming Yellow-Green Group 146B with purple coloration. Leaflet color on floral stem: Yellow-Green Group 147A on the upper surfaces and Yellow-Green Group 147B on the under surfaces. Leaflet color of mature wood: Yellow-Green Group 147B on the upper surfaces, and Yellow-Green Group 147B and 147C on the under surfaces.

Inflorescence:

*Number of flowers*.—Generally one per stem when grown under forced greenhouse conditions.

*Peduncle*.—Erect, medium stiff, green and sometimes brown on one side if the weather is cold, possesses some hairs, commonly approximately 8 to 10.5 cm. in length (approximately 9 cm. in length on average).

*Sepals*.—Configuration: of the five sepals three commonly exhibit no extensions, one commonly exhibits a very weak extension, and one commonly exhibits a weak extension. The sepal length commonly ranges from 20 to 66 mm. Color: on the upper surface Yellow-Green Group 146A, and Yellow-Green Group 147C on the under surface. Sometimes one sepal resembles a leaflet that on the upper surface is Yellow-Green Group 147A and on the under surface is Yellow-Green Group 147B.

*Buds*.—Shape: ovate. Size before calyx breaks: the bud lengths are approximately 20 to 24 mm., with an average length of approximately 22 mm. Color as calyx breaks: deep pink, Red Group 50A with some white stripes. Size as petals open (second row): approximately 36 to 42 mm., with an average length of approximately 38 mm. Color as petals open (second row): inside: pink, Red Group 52A striped with white. outside: pink, Red Group 52A and 52B striped with white.

*Flower*.—Time: early flowering. Shape: double. Form: round to irregularly rounded when viewed from above, flattened convex at the upper part when viewed from the side, and flattened convex at the lower part when viewed from the side. Diameter: medium to large, approximately 8.2 to 10.2 cm., and approximately 9 cm. on average, with a standard deviation of 0.5 cm. Petal number: commonly approximately 40 to 48, and an average of approximately 42. Petal size (second row from outside): the length is approximately 44 to 52 mm. with a mean of approximately 48 mm., and a standard deviation of 0.2 mm.; and the width is approximately 38 to 54 mm. with a mean of approximately 45 mm., and a standard deviation of 0.5 mm. Petal shape: nearly round with weak reflexing and weak undulation of the margin. Petal color: The following description of a nearly fully open flower was made while observing a rose grown in the greenhouse during November which had been undergoing opening for 3 days. petal color (middle zone): on the inner surface pink Red Group 52A and 52B, striped with white which can tend toward salmon depending on the season, and on the outer surface pink, Red Group 52B and 52C, and sometimes striped with white. petal color (marginal zone): on the inner surface pink, Red Group 52A and 52B, striped with white which can tend toward salmon depending on the season, and on the outer surface pink, Red Group 52B and 52C, and sometimes striped with white. Petal spot at base: very small. Color of spot inner side: Yellow Group 4D. Color of spot outer side: greenish-white. Stamens: approximately 15 in number and are somewhat irregularly arranged around the pistils. Filaments: long in length and Yellow Group 8B in coloration. Anthers: medium in size, each opens at approximately the same time, and the immature coloration is Yellow-Orange Group 15C. Pollen: sparse in quantity and Yellow Group 4D in coloration. Pistils: approximately 35 in number. Styles: medium in length and Yellow Group 4D in coloration. Stigmas: pink, Red Group 52B, and generally extend above the anthers. Hips: in longitudinal section in the shape of a pitcher, and approximately 20 mm. in diameter. Seeds: small to medium in size and approximately 8 to 15 in number. Petal drop: petals detach cleanly. Fragrance: medium intensity. Lasting quality: good. When cut and placed in a vase, the flowers commonly last approximately 6 to 10 days.

Development:

*Vegetation*.—Semi-vigorous to vigorous.

*Blooming*.—Abundant and almost continuous. Under greenhouse growing conditions at Hyéres, France, approximately 140 blooms commonly are produced per square meter per year.

*Aptitude to forcing*.—Very good.

*Resistance to diseases*.—Good under greenhouse conditions as well as outside in the garden.

I claim:

1. A new and distinct variety of Hybrid Tea rose plant characterized by the following combination of characteristics:

(a) from a physical point of view forms green mature wood, assumes a bushy growth habit, and forms attractive pink striped with white double flowers, and (b) from the biological point of view forms semi-vigorous to vigorous vegetation, produces flowers in abundance, exhibits the ability readily to be forced, and is very resistant to diseases when grown in a greenhouse and in the garden;

Substantially as herein shown and described

.

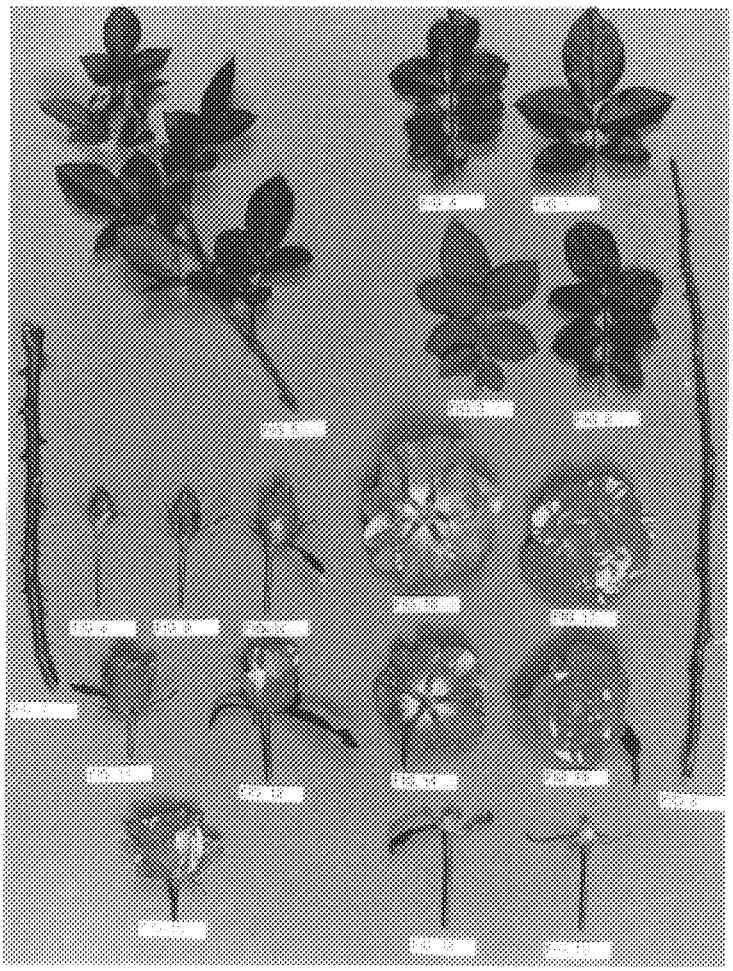

* * * * *